United States Patent [19]

Bornhop et al.

[11] Patent Number: 5,456,245
[45] Date of Patent: Oct. 10, 1995

[54] FLEXIBLE ENDOSCOPE PROBE AND METHOD OF MANUFACTURE

[75] Inventors: Darryl J. Bornhop, Bellevue, Wash.; John B. Clayton, Reno, Nev.; Allen G. Freiman, Reno, Nev.; George H. Middle, Reno, Nev.

[73] Assignee: Sofamor Danek Properties, Inc., Memphis, Tenn.

[21] Appl. No.: 123,912

[22] Filed: Sep. 20, 1993

[51] Int. Cl.[6] ............................................. A61B 1/07
[52] U.S. Cl. ..................... 600/139; 385/117; 600/182; 600/920
[58] Field of Search ................ 128/4–6; 385/115, 385/116, 117, 119; 264/1.5

[56] References Cited

U.S. PATENT DOCUMENTS

| | | | |
|---|---|---|---|
| 3,592,199 | 7/1971 | Ostensen | 128/6 |
| 3,605,725 | 9/1971 | Bentov | 128/2.05 R |
| 4,173,392 | 11/1979 | Ekinaka et al. | 128/6 X |
| 4,319,563 | 3/1982 | Kubota | 128/6 |
| 4,589,404 | 5/1986 | Barath et al. | 128/6 |
| 4,655,557 | 4/1987 | Takahashi | 350/445 |
| 4,684,224 | 8/1987 | Yamashita et al. | 350/445 |
| 4,736,733 | 4/1988 | Adair | 128/6 |
| 4,736,734 | 4/1988 | Matsuura et al. | 128/6 |
| 4,758,222 | 7/1988 | McCoy | 604/95 |
| 4,762,120 | 8/1988 | Hussein | 128/6 |
| 4,782,819 | 11/1988 | Adair | 128/6 |
| 4,784,144 | 11/1988 | Ono et al. | 128/6 X |
| 4,807,597 | 2/1989 | Tsuno et al. | 128/6 |
| 4,815,833 | 3/1989 | Zobel et al. | 350/445 |
| 5,009,655 | 4/1991 | Daignault, Jr. et al. | 606/7 |
| 5,042,980 | 8/1991 | Baker et al. | 606/7 |
| 5,108,368 | 4/1992 | Hammerslag et al. | 604/95 |
| 5,143,435 | 9/1992 | Kikuchi | 362/32 |
| 5,188,093 | 2/1993 | Lafferty et al. | 128/6 |
| 5,190,028 | 3/1993 | Lafferty et al. | 128/6 |
| 5,318,526 | 6/1994 | Cohen | 128/4 X |

FOREIGN PATENT DOCUMENTS

WO92/03963  3/1992  WIPO ........................ A61B 1/00

*Primary Examiner*—Richard J. Apley
*Assistant Examiner*—John P. Leubecker
*Attorney, Agent, or Firm*—Woodard, Emhardt, Naughton, Moriarty & McNett

[57] ABSTRACT

A flexible endoscopic probe includes a fiber optic image guide, a lens adhered to the distal end of the fiber optic image guide, and one or more fiber optic illumination fibers surrounding the image guide and terminating at the distal end of the probe. During manufacture, a mask tube is placed at least partially over the lens so that a masking material can be injected and cured. A retaining tube is disposed around the illumination fibers and a temporary tube is slid over the retaining tube so that a potting material can be injected into the spaces between the fibers, the image guide, and the retaining tube. The temporary tube is then removed, the distal end is ground and polished, and the masking material is removed from the lens.

12 Claims, 4 Drawing Sheets

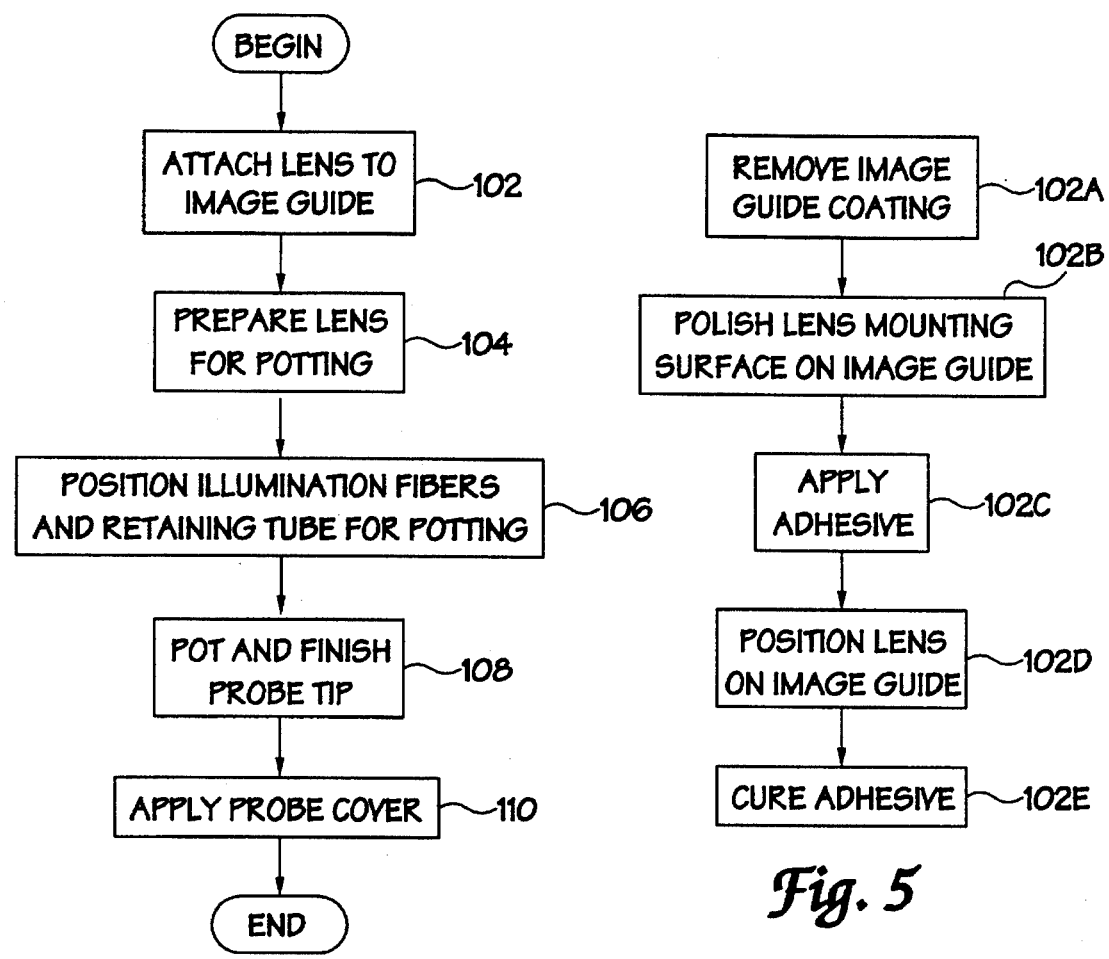
Fig. 4
Fig. 5
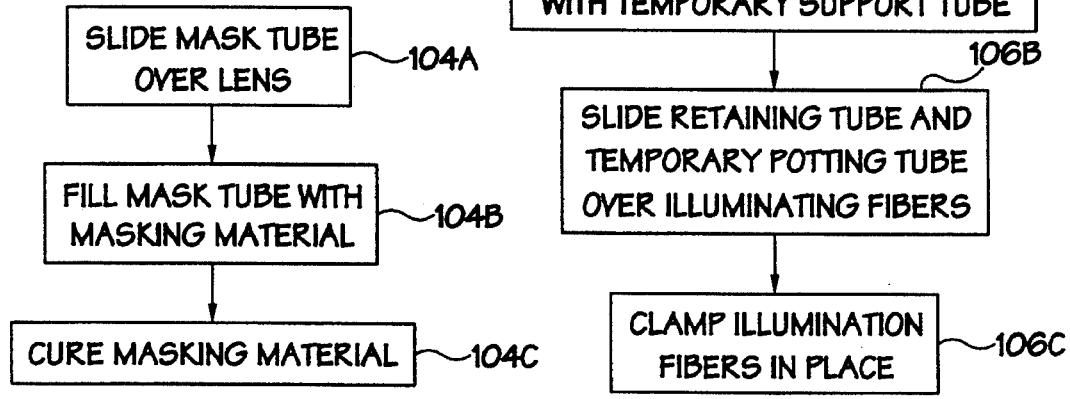
Fig. 6
Fig. 7

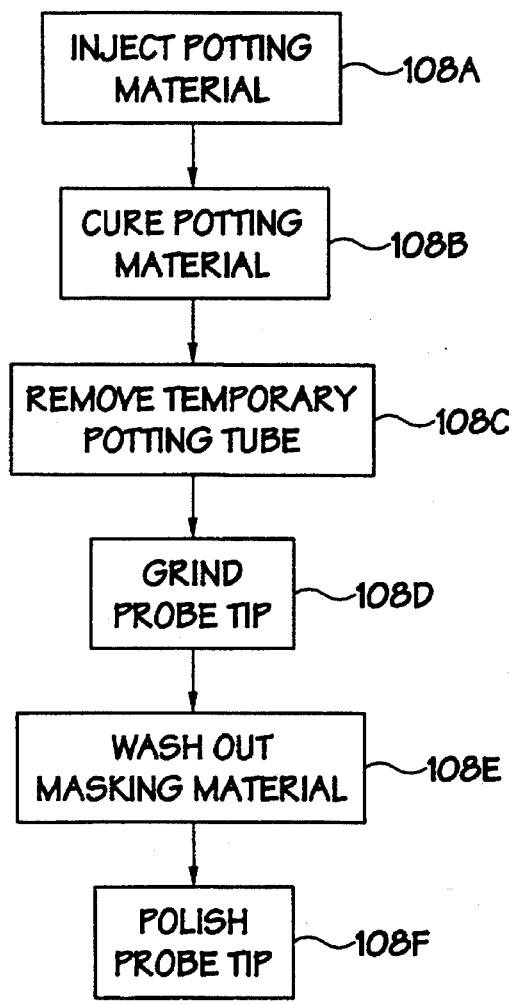
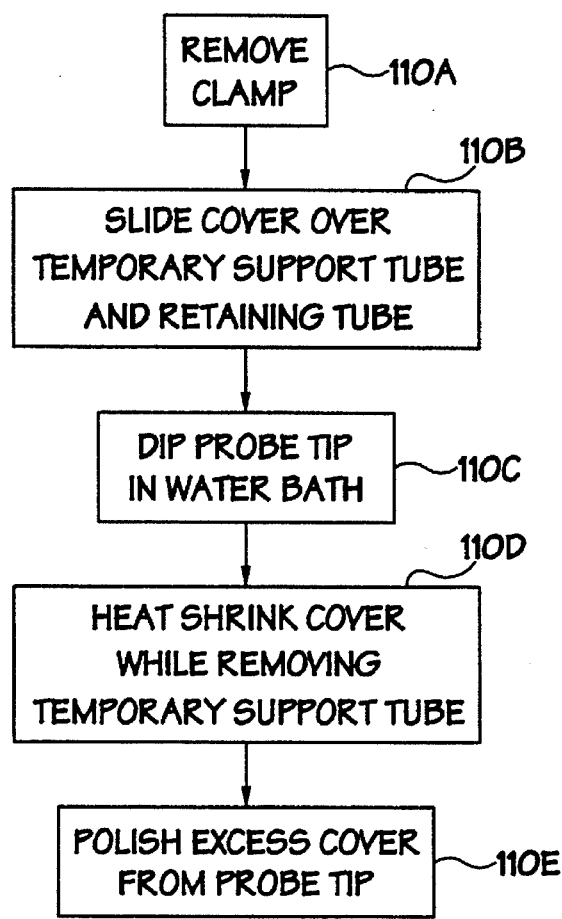
Fig. 8
Fig. 9

FLEXIBLE ENDOSCOPE PROBE AND METHOD OF MANUFACTURE

FIELD OF THE INVENTION

The present invention relates generally to medical diagnostic devices. More particularly, the present invention relates to devices used during endoscopic procedures. The present invention particularly, though not exclusively, relates to fiber optic, flexible endoscope probes and their method of manufacture.

BACKGROUND OF THE INVENTION

Modern surgical procedures attempt to minimize the invasive aspects of surgery. This is the result of the widely accepted belief that patient discomfort, overall recovery time, as well as the likelihood of post-surgical complications are generally proportional to the invasiveness of the particular procedure.

One way to reduce the invasiveness of surgical procedures such as exploratory surgery is through the use of endoscopes. Endoscopy is a surgical procedure where a thin scope is placed into the person being examined. Some specific examples include laparoscopy, where a scope is placed into the abdominal cavity, esophascopy, where the scope is placed into the esophagus, and arthroscopy, where the scope is placed into a joint.

Using endoscopes, the surgeon is able to view the interior of the person's body without the necessity of making a large incision. Instead, the endoscope, which includes a thin, insertable probe, requires only a small incision or hole into which the probe is inserted. It is the reduced trauma at the entry point which results in the reduced recovery time and reduced post-surgical complications such as infections or ruptured suture lines. Reduced trauma results because both the skin and the musculature are only minimally disturbed.

The rapidly expanding uses for endoscopy require new types of instruments which are minimally invasive. For example, in an esophascopy procedure which seeks to allow a surgeon to inspect a person's esophagus and/or stomach, the probe of the esophascope is placed into the esophagus and/or into the stomach.

Typical esophascopes are structurally representative of other types of endoscopes. For example, the probe portion typically includes a relatively rigid outer tube which contains an image guide as well as a light source. The image guide and light source are often optical fibers. The light source is used to illuminate the area adjacent the tip of the probe of the scope. Light reflected by objects is picked up by a lens which is also at the tip of the probe. The lens then directs the reflected light into the image guide which transfers the light to a video camera or other imaging means.

Importantly, it is the rigid outer tube which contains the components comprising the probe of the esophascope. Moreover, the outer tube cooperates with the other components to keep the lens fixed in front of the image guide. As noted above, the outer tube is typically relatively rigid. For most applications, this rigidity is beneficial to allow the probe to be forced into the portion of the body being viewed.

New applications of endoscopy have indicated that this rigidity is not always required, and is sometimes detrimental. For example, during esophascopy, a tool placed into the esophagus has a relatively large lumen in which to travel. Moreover, it is common to place an intubation tube into the esophagus. Accordingly, a rigid probe is not required to advance the tool through the esophagus. A scope having a flexible probe could be used by allowing the flexible probe to follow the curvatures of either the esophagus or the intubation tube.

Similarly, new exploratory surgical procedures are being envisioned where a flexible scope could be inserted into the vertebral canal. Once in the canal the scope could be used to inspect disc or nerve damage. A key limitation on these surgical techniques is the flexibility of the scope probe. Without sufficient flexibility, the likelihood of unintended trauma is too great to perform the endoscopy procedure.

There are also situations where a surgeon may have the tool enter the body in a first direction, but wish to view in a second direction. This is often the case where bones or organs cannot be moved out of the path of the scope. In these situations, a rigid scope cannot provide the desired body entry and views. This is especially true where endoscopy is used to view the inside of the spinal column.

In light of the above, it is an object of the present invention to provide a flexible fiber optic scope. It is also an object of the present invention to provide a scope which is sufficiently flexible to allow biasing of the scope tip, with the aid of a deflecting catheter, to provide a greater degree of viewing once the probe is placed within the body. Still further, it is an object of the present invention to provide an endoscope fiber optic bundle and lens system which can be used with or without a deflecting catheter. It is also an object of the present invention to provide an endoscope which can be scaled down to an outside diameter of 1 mm or less and still possess the required flexibility. Further, it is an object of the present invention to provide an endoscope which is relatively inexpensive to manufacture and comparatively easy and cost effective to use.

SUMMARY OF THE INVENTION

A flexible fiber optic endoscope probe is provided which has increased flexibility. The primary element of the probe is a standard fiber optic bundle which includes an image guide, and one or more protective coatings. The image guide is the image transmission portion of the bundle. The one or more protective layers or coatings provide protection for the image guide and prevent unwanted peripheral light from entering the fiber.

The proximal end of the fiber optic bundle is connectable to any of a number of imaging means such as a video camera and CRT display. The distal end of the bundle requires a lens to receive light reflected by the objects being viewed and to direct that light into the fiber optic image guide. To accomplish this, an objective lens is attached to the distal end of the fiber optic image guide.

In order to maintain maximum flexibility, especially near the tip of the probe, the present invention avoids the necessity of including a rigid tubular housing to maintain the lens in position in front of the image guide of the fiber optic bundle. To accomplish this, the lens of the present invention is fixably attached to the end of the fiber optic image guide using an adhesive. To prevent disengagement at the joint between the lens and the image guide, additional support is required.

In the present invention, the lens and the distal end of the image guide are surrounded by illumination fibers, all of which are kept in place by a short piece of retaining tubing. An epoxy mixture, also known as potting material, is injected into the spaces between and around the image guide/lens and the illumination fibers. When the mixture cures, the combination of the retaining tube and the epoxy mixture provides the necessary support to prevent detachment of the lens from the image guide. Moreover, the structure allows the scope to remain flexible along all but an extremely short portion at the very distal end.

Illumination for the scope working area is provided in the present invention by the illumination fibers. The proximal ends of the illumination fibers are attachable to a light source, and the distal ends are fixed within the tip of the probe as described above.

Depending on the application, an additional covering layer may cover the outside of the illumination fiber/image guide bundle combination to keep the components contained. To maintain the flexibility of the probe, the covering layer is typically a flexible and elastic material which contains the components by elastic contraction.

The extremely small size of the device, and the low tolerances which are required, make the method of manufacturing the present flexible endoscope critical.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a flow chart of the basic manufacturing steps for the method of manufacture of the tip of the flexible endoscope of the present invention;

FIGS. 5 through 9 are flow charts of the sub-steps within the basic manufacturing steps shown in FIG. 4.

DESCRIPTION OF PREFERRED EMBODIMENTS

Figure 1:
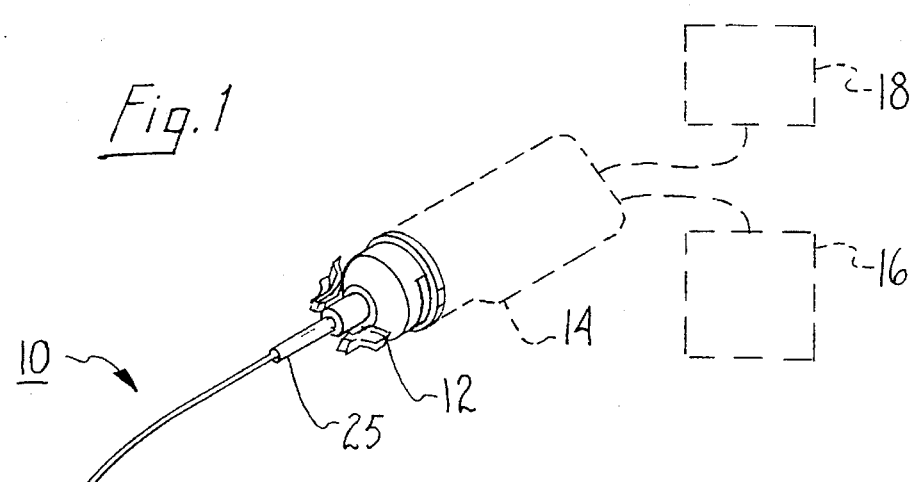
FIG. 1 is a perspective view of the flexible endoscope of the present invention.

Referring initially to FIG. 1, the probe of the flexible scope of the present invention is shown and generally designated 10. Attached at the proximal end of probe 10 is connector 12. Connector 12 is configured to allow attachment of the probe 10 to a camera 14 (shown in phantom). As is known in the art, camera 14 is connected to imaging means 16 (in phantom) and light source 18 (in phantom).

The connection between the probe and the camera 14, as well as the camera 14 and the imaging means 16 and the light source 18 are described in greater detail in U.S. Pat. No. 5,188,093, entitled "Portable Arthroscope with Periscope Optics" and U.S. Pat. No. 5,190,028 entitled "Method of Manufacturing a Disposable Arthroscope" both of which have been assigned to the assignee of the present invention and both of which are hereby incorporated by reference. It is to be appreciated that the flexible scope of the present invention could be attached to other imaging means with equal ease, simply by modifying connector 12. The required modifications are well known in the art.

The present invention is generally directed to the structure and method of manufacture of the flexible portion of the probe 10. More specifically, the structure and method of manufacture of the tip region 20 of probe 10 is critical to allow maximum flexibility of probe 10 in the tip region 20 to allow redirection of the field of vision 22 (in phantom). This flexibility must be balanced with the requirement that the lens and related tip components be prevented from disconnection during use. The present invention is for an endoscope probe with the optimum balance between flexibility and prevention of tip disconnection when deflected close to distal end 23.

Figure 2A:
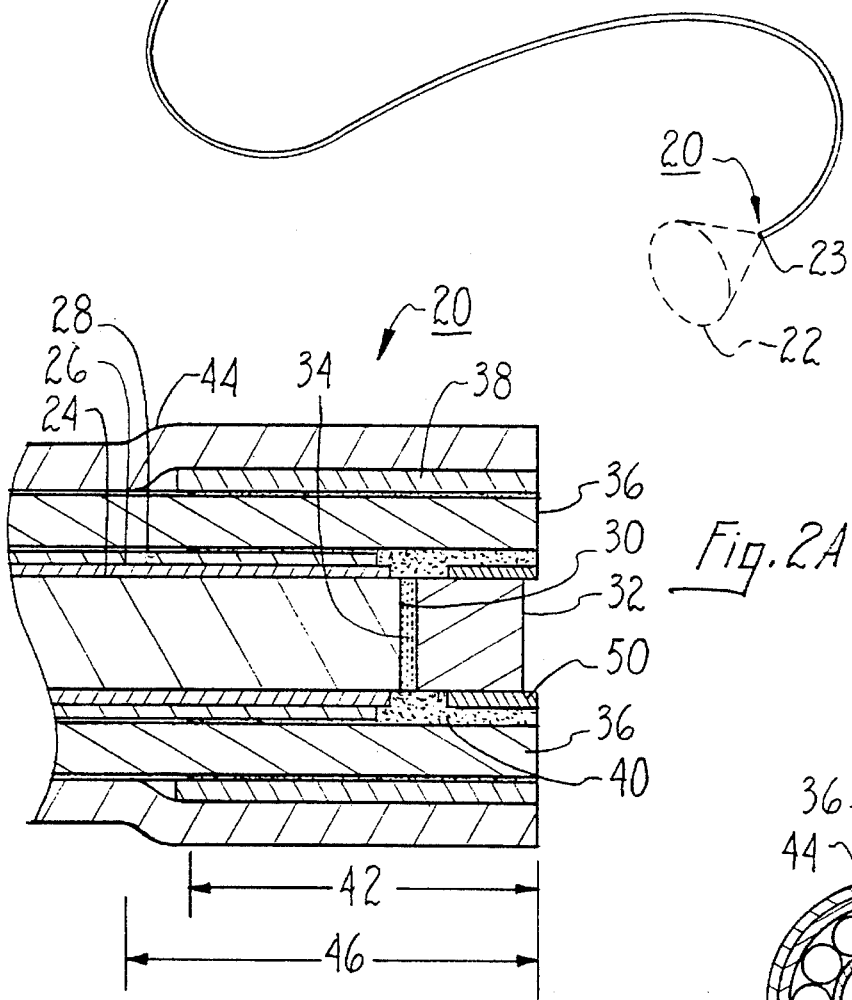
FIG. 2A is a longitudinal cross section of the distal tip of the flexible endoscope after manufacturing is complete.
Figure 2B:
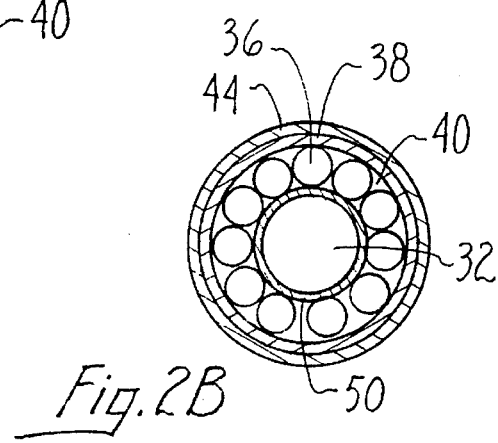
FIG. 2B is an end view of the distal tip of the flexible endoscope shown in FIG. 2A.

To better understand the structure of tip 20, attention is directed to FIGS. 2A and 2B, which show a cross-sectional view and an end view of tip 20, once it is completed. The primary structural element of tip 20 is image guide 24 which is well known in the art. As shown, image guide 24 is covered by an inner coating 26 and an outer coating 28. As can be appreciated by those skilled in the art, off-the-shelf image guides typically have one or more protective coatings. The present tip shows two coatings, 26 and 28, but the present invention is equally applicable to image guides having any number of protective coatings. As is shown in FIG. 2A, the protective coatings have been partially removed near distal end 30 to leave the peripheral surface exposed.

Attached to the distal end 30 of image guide 24 is an objective lens 32. Lens 32 can be one of several known in the art, but is preferably a gradient index (GRIN) lens. Lens 32 is fixably attached to image guide 24 using an adhesive 34 such as "Dymax 304" adhesive mixed with 1% "A1100" Silane by Union Carbide. As is apparent, the image passes through adhesive 34. Accordingly, adhesive 34 is preferably an optical adhesive having excellent transmission characteristics. As will be appreciated by those skilled in the art, other types of adhesives may be used as well.

Encircling the distal peripheral surface of lens 32 is a remnant of mask tube 50. The importance of mask tube 50 will be addressed in the disclosure of the method of manufacture below.

Illumination means are provided by one or more illumination fibers 36. The fibers are positioned along the outside of the image guide 24 and the protective coatings 26 and 28. The distal end faces of illumination fibers 36 are exposed and polished to allow maximum light transmission.

At tip 20 of the flexible scope of the present invention, a retaining tube 38 surrounds the image guide 24, the lens 32, and the illumination fibers 36. Retaining tube 38 is preferably sized to provide a snug fit such that the illumination fibers 36 are held in contact with the image guide 24 or its coatings. Retaining tube 38 is preferably constructed of a flexible plastic such as polyimide.

Despite the preferred tight fit, spaces remain inside the retaining tube 38 and between the fibers 36 and the image guide 24. These spaces are filled with a bonding, filler-type potting material 40. Preferably, potting material 40 is an epoxy based resin. One example of a suitable material is a resin/hardener material including fumed silica such as "Cab-O-Sil" colloidal silica particles by Cabot Corporation. The proportions are preferably 2 parts resin, 0.5 part EP 30HT Master Bond hardener and 0.013 part "Cab-O-Sil" colloidal silica particles. The foregoing representative mixture provides the correct amount of wicking when the mixture is injected into tip 20 during manufacturing. Preferably, potting material 40 migrates into tip 20 to a depth 42 which is less than the final finished length of retaining tube 38.

As was noted above, it is an object of the present invention to provide a flexible probe which is flexible as near as possible to its distal end. The probe of the present invention exhibits flexibility to within 5 mm of its distal end. Ultimately, it is the finished length of the retaining tube 38 and the depth of wicking of the potting material 40 which determine how much of tip 20 has decreased flexibility. Accordingly, it is desirable to minimize the finished length of tube 38 and the depth of wicking of the potting material 40. It is preferred that the ratio of the finished length of tube 38 to the length of lens 32 is no greater than 25:1.

Finally, the entire structure is covered by covering layer 44 which provides an additional environmental seal. As those skilled in the art will appreciate, it is possible to provide the present invention with alternatives to layer 44, which can affect the outside diameter and the flexibility characteristics of the probe.

To further describe the distal end of the finished probe, FIG. 2B shows an end view of the device shown in FIG. 2A. This shows the distal end of the probe assembly, illustrating the relative positions of the various elements making up the final assembly.

In manufacturing the structure described above and shown in FIGS. 2A and 2B, it is important to minimize the length 46 of the relatively inflexible portion of the probe near tip 20. Length 46 is approximately the same as the length of retaining tube 38. To achieve the minimum length 46, the method of manufacture is critical and is described in detail below.

DETAILED DESCRIPTION OF THE PREFERRED METHOD OF MANUFACTURE

Figure 3:
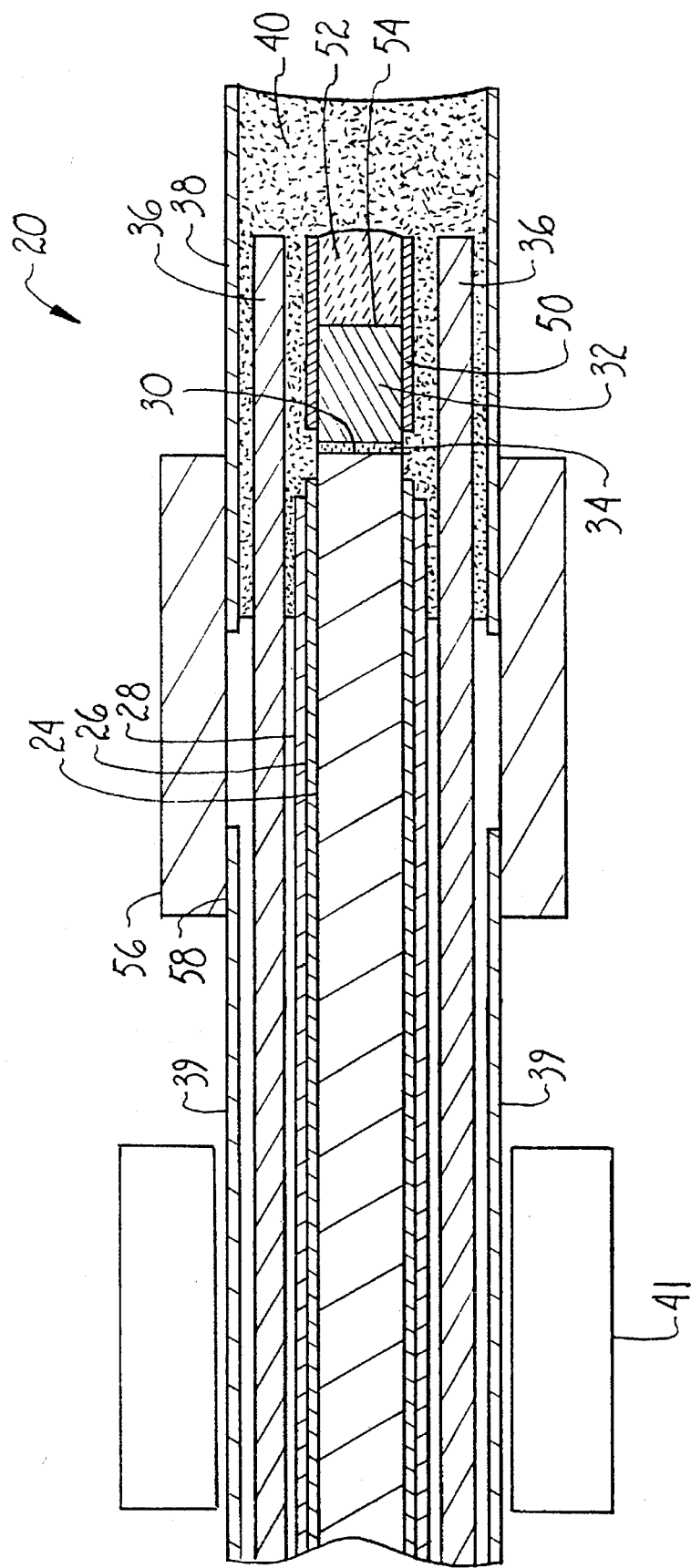
FIG. 3 is a longitudinal cross section of the distal tip of the flexible endoscope during manufacture.

To best understand the preferred method of manufacture of the endoscope probe shown in FIGS. 2A and 2B, attention is directed to FIG. 3, which shows tip 20 during the manufacturing process. Attention is also directed to FIGS. 4–9, which list the basic steps and substeps of the method of manufacture.

The basic manufacturing steps are best shown in FIG. 4, and they are as follows: attaching lens 32 to image guide 24 (step 102); preparing lens 32 for potting (step 104); positioning illumination fibers 36 and retaining tube 38 for potting (step 106); potting and finishing tip 20 (step 108); and finally, covering the probe 10 (step 110). Each of these basic steps consists of several preferred substeps, which will be described below.

Referring now to FIG. 5, the substeps of the lens attaching step 102 are shown. The first is removing a portion of the coatings from the image guide 24 (step 102A). Preferably, a sufficient length of the coatings 26, 28 should be removed to allow the end of image guide 24 to be exposed along the periphery. Then, the lens mounting surface on distal end 30 of image guide 24 is polished (step 102B). Next, adhesive 34 is applied to the image guide 24 and/or lens 32 (step 102C), and the lens 32 is positioned against the image guide 24 (step 102D). Finally, the adhesive 34 is allowed to cure (step 102E), using thermal and/or UV curing as required for the type of adhesive. See FIG. 3 for the resulting structure.

Referring now to FIG. 6, the substeps of the lens preparation step 104 are shown. Preparation of lens 32 for potting begins with sliding on mask tube 50 over at least a portion of lens 32 (step 104A), leaving a portion of mask tube 50 extending beyond distal end face 54 of lens 32. Next, the extending end of mask tube 50 is filled with masking material 52 to fully mask the distal end face 54 of lens 32 (step 104B). It is preferred that masking material 52 be a water soluble, curable material which can provide a barrier against the potting material 40, hence protecting the lens distal end face 54. The masking material is then cured (step 104C). See FIG. 3 for the resulting structure.

Referring now to FIG. 7, the substeps of the illumination fiber positioning step 106 are shown. Initially, illumination fibers 36 are arranged around the periphery of the image guide 24 and lens 32 and surrounded by temporary support tube 39 (step 106A). Temporary support tube 39 keeps illumination fibers 36 properly oriented around image guide 24 and protects them, while tip 20 of probe 10 is potted and finished. Temporary support tube 39 also assists in the application of cover layer 44, as will be explained later. As will be appreciated by those skilled in the art, the more fibers that are added, the thicker the overall diameter of the probe. On the other hand, the more fibers, the more illumination. Preferably, as many fibers as possible are added as permitted by the desired finished diameter of the probe. Fibers 36 are preferably positioned such that the distal end of each fiber extends beyond the distal end face 54 of lens 32. This is so that fibers 36 will become exposed during finishing as described later. See FIG. 3 for the resulting structure.

After the fibers 36 are placed around the image guide 24, and surrounded by temporary support tube 39, a retaining tube 38 and a temporary potting tube 56 are slid over the fibers 36 (step 106B). Temporary potting tube 56 connects temporary support tube 39 to retaining tube 38, with a small air gap between. It is sized to fit snugly around the proximal end of retaining tube 38 and the distal end of temporary support tube 39, thereby holding retaining tube 38 in place relative to the joint between image guide 24 and lens 32, during the potting step. Retaining tube 38 extends from just slightly proximally of the image guide/lens joint to just distally of the distal surface 54 of lens 32. Finally, clamp 41 is applied to temporary support tube 39, to hold illumination fibers 36, temporary support tube 39, temporary potting tube 56, and retaining tube 38 in place (step 106C). Clamping fibers 36 in place (step 106C) ensures that the assembly cannot be disturbed during the potting process.

Next, the substeps of the potting and finishing step 108 are shown in FIG. 8. The potting material 40, described above, is injected with a syringe into the distal end of retaining tube 38 (step 108A). Tube 38 extends beyond the distal end of mask tube 50, and this extension of retaining tube 38 acts as a potting material reservoir and as a guide to channel the potting material 40 into the spaces between the fibers 36, retaining tube 38 and image guide 24. See FIG. 3 for the resulting structure.

After the potting material is injected (step 108A) it is cured as required (step 108B). If the epoxy mixture described above is used, optimal curing is achieved by thermally curing the assembly in a horizontal position for 1 hr at 58° C. After curing is complete, the temporary potting tube 56 is removed from the assembly (step 108C).

Next, the tip 20 is finished by first grinding away excess material from the tip region (step 108D). Preferably, tip 20 is ground down to within 0.001–0.003 inches of the distal surface 54 of lens 32. Next, the remaining masking material 52 is washed from the distal surface 54 of lens 32 (step 108E). Then, probe tip 20 is polished (step 108F).

Finally, probe 10 is preferably covered with covering layer 44 in step 110, which includes the substeps shown in FIG. 9. Clamp 41 is removed (step 110A). Then, covering layer 44 is slid over temporary support tube 39 and retaining tube 38 (step 110B). Cover 44 is preferably a heat shrinkable tube. Next, the distal end of cover 44 is shrunk into a tight fit by dipping the tip 20 of the probe 10 into hot water (step 110C). The remainder of cover 44 is heat shrunk onto probe 10 by blowing hot air over the remainder of cover 44, while simultaneously removing temporary support tube 39 as cover 44 shrinks (step 110D), until the desired fit is obtained. Finally, any excess length of cover 44 is removed from the distal end of tip 20 by grinding or polishing (step 110E). The resulting probe tip is shown in FIGS. 2A and 2B.

While the particular flexible endoscope and method of manufacture as herein shown and disclosed in detail are fully capable of obtaining the objects and providing the advantages herein before stated, it is to be understood that they are merely illustrative of the presently preferred embodiments of the invention and that no limitations are intended to the details of construction or manufacturing methods herein shown other than as described in the appended claims.

We claim:

1. A method for manufacturing a fiber optic probe having a distal tip, comprising the steps of:
    attaching a lens to a distal end of an image guide;
    sliding a mask tube at least partially over said lens;
    filling said mask tube with a masking material;
    curing said masking material;
    positioning at least one illumination fiber alongside said image guide;
    potting said lens, said distal end of said image guide, and a distal end of said at least one illumination fiber.

2. The method as recited in claim 1 wherein said attaching step comprises the substeps of:
    polishing said distal end of said image guide;
    applying adhesive to said distal end of said image guide;
    positioning said lens to contact said adhesive; and
    curing said adhesive.

3. The method as recited in claim 1 wherein said potting step comprises the substeps of:
    forming potting material around said lens, said distal end of said at least one illumination fiber, and said distal end of said image guide:
    grinding away the potting material from said potted components at the distal tip of the probe to expose said masking material; and
    washing away said masking material.

4. The method as recited in claim 3, further comprising the step of polishing the distal tip of the probe following said washing step.

5. The method as recited in claim 3, wherein said grinding step includes grinding away said potting material and said masking material leaving a small amount of said masking material on said lens.

6. The method as recited in claim 1 wherein said positioning at least one illumination fiber step comprises the substeps of:
    surrounding said image guide with said at least one illumination fiber; and
    sliding a retaining tube over said image guide and said at least one illumination fiber.

7. The method as recited in claim 6 wherein said fixing step comprises the substeps of:
    injecting potting material into said retaining tube; and
    curing said potting material.

8. The method as recited in claim 1 further comprising the step of covering said probe with a protective layer.

9. The method as recited in claim 8 wherein said covering step comprises the substeps of:
    sliding a covering layer over said probe; and
    shrinking said covering layer.

10. The method as recited in claim 9 wherein said shrinking step comprises the substeps of:
    dipping the distal tip of said probe in a hot water bath; and
    blowing hot air over the remainder of said probe.

11. The method as recited in claim 1, further comprising:
    sliding a retaining tube over said image guide and said at least one illumination fiber; and
    introducing said potting material into said retaining tube around said lens, said distal end of said at least one illumination fiber;
    and said distal end of said image guide.

12. A method for manufacturing a fiber optic probe having a distal tip, comprising the steps of:
    attaching a lens to a distal end of an image guide;
    preparing said lens for potting;
    surrounding said image guide with at least one illumination fiber;
    sliding a retaining, tube over said image guide and said at least one illumination fiber;
    sliding a temporary tube over said retaining tube;
    injecting potting material into said retaining tube;
    curing said potting material; and
    removing said temporary tube.

* * * * *